United States Patent
Nagai et al.

(10) Patent No.: US 11,474,038 B2
(45) Date of Patent: Oct. 18, 2022

(54) METHOD FOR EVALUATING PROTECTIVE EFFECT AGAINST EXTERNAL DAMAGE TO SKIN

(71) Applicant: Shiseido Company, Ltd., Tokyo (JP)

(72) Inventors: Kouichi Nagai, Kanagawa (JP); Kei Ujimoto, Kanagawa (JP); Marianne Ayaka Touati, Kanagawa (JP); Yuko Nagare, Kanagawa (JP); Satoshi Yamaki, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 114 days.

(21) Appl. No.: 16/966,276

(22) PCT Filed: Jan. 31, 2019

(86) PCT No.: PCT/JP2019/003305
§ 371 (c)(1),
(2) Date: Jul. 30, 2020

(87) PCT Pub. No.: WO2019/151374
PCT Pub. Date: Aug. 8, 2019

(65) Prior Publication Data
US 2020/0371027 A1 Nov. 26, 2020

(30) Foreign Application Priority Data

Feb. 5, 2018 (JP) .............................. JP2018-018269
Aug. 10, 2018 (JP) .............................. JP2018-151682

(51) Int. Cl.
*G01J 3/00* (2006.01)
*G01N 21/59* (2006.01)
*G01N 33/15* (2006.01)

(52) U.S. Cl.
CPC .............. *G01N 21/59* (2013.01); *G01N 33/15* (2013.01)

(58) Field of Classification Search
CPC .. G01N 21/314; G01N 21/33; G01N 21/3504; G01J 3/10; G01J 3/42

(Continued)

(56) References Cited

U.S. PATENT DOCUMENTS

2013/0169951 A1 7/2013 Miura et al.
2013/0231401 A1* 9/2013 Hiruma .................. A61Q 19/02
514/772.4

(Continued)

FOREIGN PATENT DOCUMENTS

CN 102179011 A * 9/2011
CN 102179011 B * 3/2013

(Continued)

OTHER PUBLICATIONS

International Search Report and Written Opinion dated Apr. 9, 2019, in PCT/JP2019/003305, with English translation.

(Continued)

*Primary Examiner* — Md M Rahman
(74) *Attorney, Agent, or Firm* — Foley & Lardner LLP

(57) ABSTRACT

The purpose of the present invention is to newly provide a method with which it is possible to appropriately evaluate the protective effect of an external preparation for skin such as a sunscreen cosmetic, particularly to evaluate how a UV-ray protective effect is affected by heat. This evaluation method is characterized by including (1) a step for forming a coating film of an external preparation for skin on a substrate, (2) a step for heat-treating the coating film of the external preparation for skin, and (3) a step for measuring the UV-ray protective effect of the heat-treated coating film of the external preparation for skin. The heat treatment is preferably carried out for at least one minute at a temperature of 30-70° C. The step for measuring the UV-ray protective effect preferably includes at least one selected from testing methods that involve comparing some kind of UV-ray protective effect with SPF measurement, UVAPF or PFA measurement, critical wavelength measurement, absorbance measurement, and transmittance measurement. This evaluation method can also be performed in vivo or in vitro.

16 Claims, 3 Drawing Sheets

(58) Field of Classification Search
USPC .......................................................... 356/51
See application file for complete search history.

(56) References Cited

U.S. PATENT DOCUMENTS

2015/0308945 A1    10/2015   Hanyu et al.
2016/0025481 A1     1/2016   Stanfield et al.

FOREIGN PATENT DOCUMENTS

| JP | 2006-028335 | A |   | 2/2006 |
|----|-------------|---|---|--------|
| JP | 2007-284516 | A |   | 11/2007 |
| JP | 2012-063323 | A |   | 3/2012 |
| JP | 5184031     | B2 | * | 4/2013 |
| JP | 2014-071007 | A |   | 4/2014 |
| JP | 2015178489  | A | * | 10/2015 |
| JP | 2017-146211 | A |   | 8/2017 |
| WO | WO-2010/095116 | A1 |  | 8/2010 |
| WO | WO-2016/068300 | A1 |  | 5/2016 |
| WO | WO-2016/138249 | A1 |  | 9/2016 |

OTHER PUBLICATIONS

Mizuno, Makoto, "Current Conditions of Sun Protection Test Methods for Sunscreen Products," Journal of Society of Cosmetic Chemists of Japan, Apr. 2013, 47(4):271-277, with English abstract on last page.

Shiseido Information Letter, "Countermeasures against UV rays to protect beautiful skin," Mar. 26, 2015, 92(2015):1-9.

Supplementary European Search Report dated Sep. 13, 2021 in EP 19748439.7.

* cited by examiner

METHOD FOR EVALUATING PROTECTIVE EFFECT AGAINST EXTERNAL DAMAGE TO SKIN

CROSS-REFERENCE TO RELATED APPLICATIONS

This application is the U.S. National Stage of PCT/JP2019/003305, filed Jan. 31, 2019, which claims priority to JP 2018-018269, filed Feb. 5, 2018 and JP 2018-151682, filed Aug. 10, 2018.

TECHNICAL FIELD

The present invention relates to an evaluation method of a protective effect of an external preparation for skin against external damage to skin, especially an evaluation method of an ultraviolet (UV) protective effect (or UV blocking effect) of a sunscreen cosmetic and the like. More specifically, the present invention relates to an evaluation method which makes it possible to appropriately specify a change in the UV protective effect due to heat by intentionally incorporating a heat treatment step, which has not been considered in conventional methods for evaluating UV protective effects.

BACKGROUND ART

Light rays such as ultraviolet (UV) rays, blue light, visible rays, and infrared rays are known to have an influence on skin, and various external preparation for skins (including skin care cosmetics and the like) exhibiting an effect of reducing influences of these rays on skin have been known.

Among them, sunscreen cosmetics exhibit an effect of suppressing baneful influences on skin by decreasing the dose of UV rays reaching to skin with the cosmetics applied thereon, by virtue of the action of an ultraviolet (UV) absorber or an ultraviolet (UV) scattering agent blended in the cosmetics.

Sun Protection Factor (SPF) is most widely known as an index of UV protective effects of sunscreen cosmetics, and the UV protective effects are identified as SPF values (for example, "SPF 30" and the like). In Japan, Protection Factor of UVA (PFA) or UVA Protection factor of product (UVAPF) is used for UV rays in a UVA region, and a degree of the UVA protective effect of a product is identified in Protection grade of UVA (PA) classification ("PA++" and the like) based on the value of PFA or UVAPF. In the United States, critical wavelength (CW), which indicates a balance between protective effects against UVA and UVB, is used.

In-vivo determination of SPF (2010) and in-vivo determination of sunscreen UVA protection (2011) have been successively established by International Organization for Standardization (ISO) as International Standards (IS) for measurement methods of UV protective effects of sunscreen cosmetics. In Japan, while Japan Cosmetic Industry Association (JCIA) established an independent standard ahead of ISO, an internationally harmonized measurement method into which the above-described international standards are incorporated has been established at present (Non-Patent Document 1).

On the other hand, since cooperation of a subject having a specific skin type is essential and a lot of time and cost are taken for the in-vivo measurements described above, various methods for simply measuring UV protective effects of sunscreen products in-vitro have also been proposed. For example, Patent Document 1 describes an in-vitro measurement method and an in-vitro measurement device which provide an SPF value highly correlating with a value obtained in in-vitro measurement. In addition, a method and a device for evaluating a UV protective effect based on a predicted SPF value obtained in-vitro have also been developed (Patent Document 2).

Cosmetics exerting a high UV protective effect in a wide wavelength region from UVA to UVB have been required recently so as to suppress bad influences of UV rays on skin, and sunscreen products targeting SPF of 50 or higher (50+) and PA++++ have been commercially available, for example.

While the UV protective effects of sunscreen products are exerted by an UV absorber or an UV scattering agent (titanium oxide, zinc oxide, and the like) blended therein, some UV absorbers deteriorate in UV absorbing performance due to light irradiation (for example, see Patent Document 3), and UV scattering agents may outflow through contact with water to deteriorate protective performance. Accordingly, methods for testing optical stability and waterproofness of a UV protective effect have been studied also in ISO (Non-Patent Document 1).

Various measures have been proposed to suppress optical deterioration of a UV protective effect (Patent Document 3), and a sunscreen cosmetic having such an innovative property that the UV protective effect thereof is not deteriorated even when the sunscreen cosmetic is brought into contact with water, but on the contrary, the protective effect improves has been developed (Patent Document 4) in regard to waterproofness.

However, as for heat, while there is an example in which an influence of heat on emulsion stability of an emulsion cosmetic including a sunscreen cosmetic is studied (Patent Document 5), for example, a change in a UV protective effect due to heat has not been studied so far.

CITATION LIST

Patent Document

Patent Document 1: JP 3337832 B
Patent Document 2: JP 4365452 B
Patent Document 3: JP 2010-150172 A
Patent Document 4: WO 2016/068300 A
Patent Document 5: JP 4397286 B

Non-Patent Document

Non-Patent Document 1: Journal of the Society of Cosmetic Chemists of Japan Vol. 47, No. 4, pp. 271-277, 2013

SUMMARY OF INVENTION

Technical Problem

Accordingly, an object of the present invention is to newly provide a method capable of appropriately evaluating an influence of heat on a protective effect of an external preparation for skin against rays of light having an influence on skin, especially an influence of heat on a UV protective effect of a sunscreen external preparation for skin.

Solution to Problem

The present invention provides an evaluation method for an external preparation for skin such as a sunscreen cosmetic, the evaluation method including:

(1) a step of forming a coating film of an external preparation for skin on a base body;

(2) a step of subjecting the coating film of the external preparation for skin to heat treatment; and (3) a step of measuring a protective effect, preferably a UV protective effect of the coating film of the external preparation for skin subjected to the heat treatment against a ray of light having an influence on skin.

The above-described step (1) and step (2) may be simultaneously performed.

The step of measuring the UV protective effect preferably includes at least one selected from the group consisting of SPF measurement, UVAPF or PFA measurement, critical wavelength measurement, absorbance measurement, transmittance measurement, and a test method comparing any UV protective effect.

Advantageous Effects of Invention

According to the evaluation method of the present invention, an influence of heat on a ray (UV ray or the like) protective effect of an external preparation for skin such as a sunburn-preventer (sunscreen) can be appropriately evaluated.

DESCRIPTION OF EMBODIMENTS

An evaluation method of an external preparation for skin, such as a sunscreen cosmetic, according to the present invention includes:

(1) a step of forming a coating film of an external preparation for skin on a base body;

(2) a step of subjecting the coating film of the external preparation for skin to heat treatment; and (3) a step of measuring a protective effect of the coating film of the external preparation for skin subjected to the heat treatment.

The "external preparation for skin" in the present disclosure includes, in addition to a sunscreen cosmetic, a makeup cosmetic, a hair care product, and the like. In addition, the "protective effect" in the present disclosure includes, in addition to a protective effect against UV rays, a protective effect against rays of light such as blue light, visible rays, infrared rays, and the like.

Figure 1:
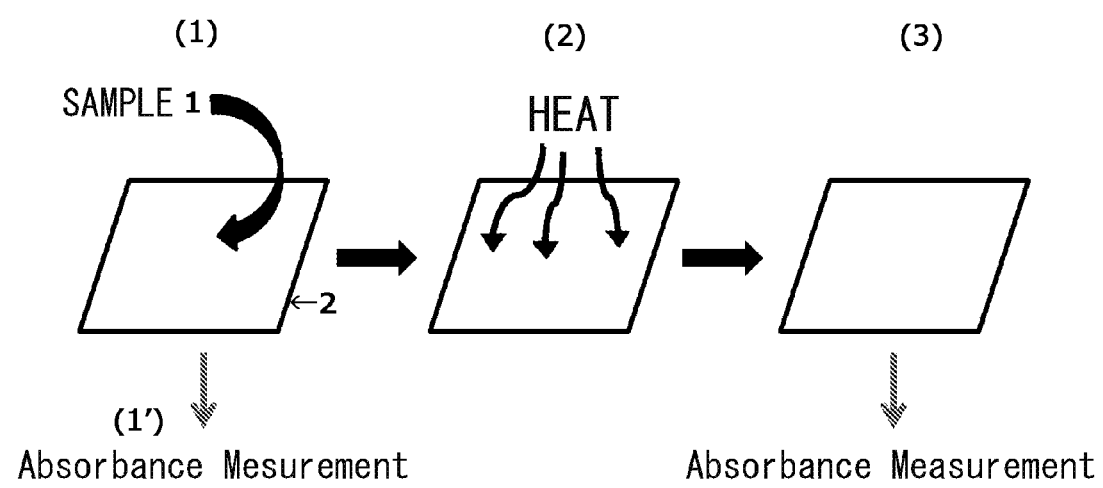
FIG. 1 is an explanatory diagram illustrating an outline of an evaluation method of the present invention.

FIG. 1 is a diagram for explaining an outline of the evaluation method of the present invention.

In step (1), a predetermined amount of a sample (test material) 1 of a sunscreen external preparation for skin is applied to a base body 2 and optionally drying the sample 1 to form a coating film of the sample 1 on the base body 2.

(1') a step of measuring a UV protective effect (absorbance or the like) of the formed sample coating film before heating may be optionally included.

In subsequent step (2), heat is applied to the sample coating film formed in step (1). This heating step (2) may be performed by applying heat to the sample coating film formed on the base body, or by heating the base body to a predetermined temperature in step (1) and applying the sample thereto to heat the sample coating film (that is, step (1) and step (2) are simultaneously performed).

Finally, the UV protective effect (absorbance or the like) of the sample coating film subjected to heat treatment is measured in step (3).

The evaluation method of the present invention may include steps of: providing another sample (second sample) of the same sunscreen external preparation for skin as the above-described sample; applying the second sample to another area of the base body and optionally drying the second sample to form a second sample coating film (step 1A); preferably keeping the second sample coating film at ordinary temperature without subjecting the second sample coating film to heat treatment (step (2)) (step 2A); and measuring a UV protective effect of the unheated second sample coating film in step (3) (step 3A). Furthermore, (4) a step of comparing the UV protective effect of the heated sample coating film and the UV protective effect of the unheated second sample coating film may be included.

Meanwhile, when measurement of the UV protective effect of the sample coating film before being heated (step (1')) is carried out in the above-described step (1), (4') a step of comparing the UV protective effect before being heated and the UV protective effect after being heated measured in step (3) may be included.

The evaluation method of the present invention can be conducted in-vivo or in-vitro.

Detailed description is as follows.

(A) In-Vivo Evaluation Method

Figure 2:
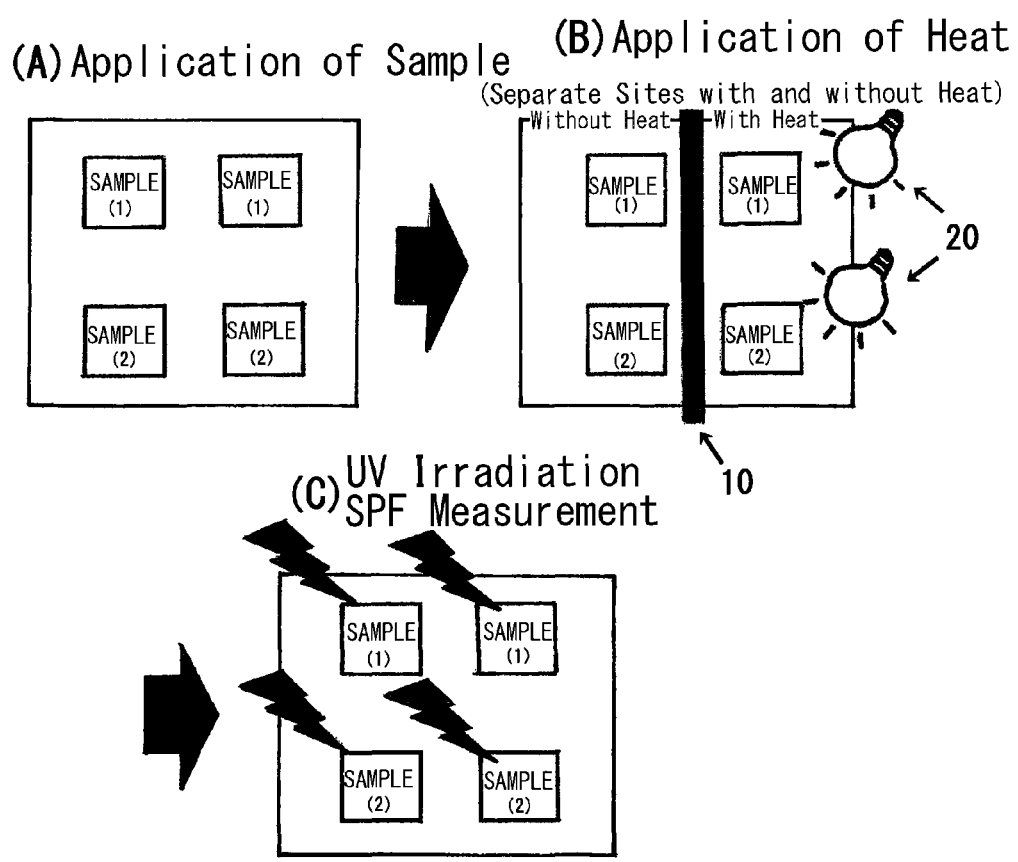
FIG. 2 is an explanatory diagram illustrating an example of the evaluation method of the present invention appropriate for being conducted in-vivo.

FIG. 2 is a diagram for explaining an example of the evaluation method of the present invention conducted in-vivo.

The following example is a case where SPF measurement is employed as UV protective effect measurement. See "Japan Cosmetic Industry Association Standard SPF Test Method (revised in 2011)" and "ISO24444 Cosmetics-Sun protection test methods-In vivo determination of the sun protection factor (SPF)" for details of the SPF measurement method.

A sample of a sunscreen external preparation for skin is firstly applied to a predetermined site of a base body (skin of a subject), and the sample is optionally dried to form a sample coating film (FIG. 2(A)). At this time, it is preferable that the same sample be applied to at least two areas of the base body to form coating films. In FIG. 2, two kinds of sample (1) and sample (2) are each applied to two areas.

The above-described predetermined site is not particularly limited and is preferably set within a region between the shoulder blade and the waist of the back of the subject.

As shown in FIG. 2(B), heat treatment of applying heat to at least one of the sample coating films formed on at least two areas of the base body is subsequently carried out.

It is preferable to take a measure to prevent heat transfer from the site to be heated ("heating site": the right side in FIG. 2(B)) to the site not to be heated ("non-heating site": the left side in FIG. 2(B)) prior to the heat treatment. For example, it is preferable that the non-heating site be covered with a heat-insulating or heat-shielding member such as a towel or aluminum foil, or a shielding material 10 be provided in between the heating site and the non-heating site. When a region between the shoulder blade and the waist of the back of the subject is used as the above-described predetermined site, the shielding material 10 is preferably disposed along the backbone of the subject but is not limited thereto.

The shielding material 10 shields heat (infrared rays) emitted from an infrared lamp 20 illustrated in FIG. 2(B), for example, to prevent heat from reaching the non-heating site. A plate-like member made of a material having low thermal conductivity, for example, a foamed-type heat-insulating material such as urethane foam, a fibrous heat-insulating material such as cork and cellulose fibers, or the like is preferably used as the shielding material 10.

A heating method is not particularly limited, and infrared ray irradiation using an infrared lamp 20, or the like is preferably used, for example.

In addition, the temperature of the heating site is preferably checked by a thermography, a thermometer, or the like during heat treatment so as to confirm that the temperature of the heating site is kept at the predetermined temperature. It is preferable to also confirm that the temperature at the non-heating site is not changed by a thermography, a thermometer, or the like at the same time.

Heat treatment is preferably carried out at a temperature higher than a body surface temperature and equal to or lower than about 45° C. The body surface temperature may vary according to an environmental temperature and a state of the subject (febrile or afebrile, before or after exercise, and the like). Preferably, it is preferable that a healthy person (afebrile person) be selected as the subject, and a body surface temperature of the subject having rested for a predetermined time (for example, 10 minutes, 30 minutes, one hour, or the like) in an environment in which the temperature is adjusted to an appropriate temperature (for example, 25° C.) be adopted. The body surface temperature is usually about 30° C. or higher and becomes 32° C. or higher, 35° C. or higher, or 37° C. or higher in some cases. Heat treatment is preferably carried out at a temperature at least 1° C. or higher, preferably 2° C. or higher, and more preferably 3° C. or higher than the body surface temperature. An upper limit of the heat treatment temperature is preferably about 45° C. or lower in consideration of a temperature at which the sunscreen cosmetic is actually used (for example, the body surface temperature under irradiation with sunlight in the summer season is about 40° C. and becomes 41° C. to 45° C. in some cases), safety of the subject, and the like.

A heating time is preferably one minute or longer and more preferably 10 minutes or longer in order to accurately evaluate the influence of heat. An upper limit of the heating time is not particularly limited and is usually 60 minutes or shorter and preferably 30 minutes or shorter.

After the completion of the heat treatment, the sample coating films are left until the temperature of the heating site is decreased and return to a normal skin temperature. Preferably, the temperatures of the heating site and the non-heating site are confirmed to become equal to each other using, a thermography, a thermometer, or the like.

Finally, the shielding material 10 or the like is optionally removed, and SPF of each sample coating film is subsequently measured (FIG. 2(C)).

Specifically, the sample-coated part and an uncoated part adjacent to the sample-coated part in the tested site are irradiated with UV rays, and the minimum UV ray dose (MED) initially evoking clearly bounded slight erythema in an area equal to or more than two thirds of the irradiated part is determined after a lapse of a predetermined time (usually 16 to 24 hours). The MED at the sample-coated part is referred to as MEDp, and the MED at the uncoated part is referred to as MEDu.

The SPF (also referred to as SPFi) of the sample for the subject is calculated according to the following equation using the MEDpi and MEDui determined for the subject.

$$SPFi = (MEDpi)/(MEDui) \quad \text{[Expression 1]}$$

The above steps are performed on a plurality of subjects, and an arithmetical mean value (decimal places are rounded down) of SPFi values obtained from the subjects is regarded as the SPF of the sample.

In the evaluation method of the present invention conducted in-vivo, when PA measurement is employed as a measurement method of the UV protective effect, steps (1) and (2) are performed as with the above-described manner, and UVAPF or PFA which is preferably measured in accordance with Japan Cosmetic Industry Association Standard UVA Protective Effect Test Method (revised in 2012) or ISO24442 is calculated instead of the SPF measurement in step (3), and the UV protective effect can be identified as PA according to the following classification.

TABLE 1

| UVAPF | Classification identification |
|---|---|
| 2 or more and less than 4 | PA+ |
| 4 or more and less than 8 | PA++ |
| 8 or more and less than 16 | PA+++ |
| 16 or more | PA++++ |

In in-vivo measurement in which SPF and UVAPF are calculated by irradiating the skin of the subject with UV rays, it is preferable to fully explain the purpose and contents of measurement by presenting an explanation document to the subject and obtain written consent in advance.

In addition, the subject is recommended not to expose the portion to be tested (back) to sunlight at least four weeks before being subjected to SPF measurement from medical and ethical considerations. In view of this, it is preferable not to carry out UV protective effect measurement before heat treatment (step (1')).

(B) In-Vitro Evaluation Method

A resin substrate such as a PMMA, nylon, or acrylic plate and a plate of an inorganic material such as glass and quartz can be used as the base body in an in-vitro evaluation method according to the present invention. Further, the base body may be an organic substance such as paper. A skin-substitutive membrane (also referred to as an "S-plate": see Japanese Patent No. 4453995) comprised of a PMMA plate having a surface on which a groove having a V-letter shape is provided, or the like is preferably used.

In step (1) illustrated in FIG. 1, a predetermined amount of a sample (test material) of a sunscreen external preparation for skin is applied to the surface of the base body, and the sample is optionally dried to form a sample coating film.

Thereafter, in step (2), the base body on which the sample coating film is formed is heated. The above-described infrared irradiation may be employed as a heating method, but heating may be carried out by leaving the base body on which the sample coating film is formed to stand in a thermostatic chamber in which the temperature is adjusted to a predetermined temperature. Alternatively, step (1) and step (2) can also be simultaneously performed by forming the sample coating film on the base body which is heated to a predetermined temperature in advance.

A heating temperature preferably falls within a range of 30° C. to 70° C. When the heating temperature exceeds 70° C., a problem such as melting of the substrate made of resin may arise. The heating temperature is not particularly limited as long as it is a temperature falling within the above range and can be 32° C. or higher, 35° C. or higher, 37° C. or higher, or 40° C. or higher, for example, and heat treatment may be carried out at a temperature of 65° C. or lower, 60° C. or lower, 55° C. or lower, or 50° C. or lower.

A heating time is preferably one minute or longer and more preferably 10 minutes or longer in order to accurately evaluate the influence of heat. An upper limit of the heating time is not particularly limited and is usually 60 minutes or shorter and preferably 30 minutes or shorter.

It is preferable that a coating film be formed on each of a plurality of substrates using the same sample at the same amount in the above-described step (1), at least one of the coating films be subjected to heat treatment in step (2) (heated sample), and the rest (non-heated sample) be kept at ordinary temperature.

After the completion of step (2), the sample coating films are preferably left until the temperatures of the base bodies return to ordinary temperature, and an absorbance at a predetermined wavelength (UVA or UVB region) of the sample coating film of each base body is measured (step (3)).

In the present invention, "absorbance measurement" includes absorbance measurement at a single wavelength (UV region) and absorbance measurement over a predetermined wavelength region (critical wavelength measurement is also included).

SPF or UVAPF (or PFA) may be calculated on the basis of the absorbance measured in step (3) and used as an index of the UV protective effect.

In addition, a change in the UV protective effect due to heat can be detected by comparing the UV protective effect of the "heated sample" and the UV protective effect of the "non-heated sample" in step (3).

Furthermore, as changes in absorbance of the "heated sample" and the "non-heated sample" between step (1) and step (3) become clear by providing (1') a step of measuring an absorbance of each sample coating film formed in step (1), by virtue of referring to these values, a change due to heat can be accurately grasped, with a change in the UV protective effect not resulting from heat but resulting from variation with time, for example, compensated.

In the in-vivo measurement and the in-vitro measurement, it is preferable that heat treatment (step (2)) be performed in an environment shielded from UV rays from the viewpoint of eliminating influences of factors other than heat.

As described in detailed above, the evaluation method of the present invention can directly compare the UV protective effect of the heated sample and the UV protective effect of the non-heated sample for the same sunscreen external preparation for skin (cosmetic) sample regardless of whether the evaluation method is conducted in-vivo or in-vitro. A test method of comparing UV protective effects includes a test method using photosensitive paper and a test method utilizing a substance whose color changes by UV irradiation.

Accordingly, the evaluation method of the present invention can be used as a method for screening a sunscreen external preparation for skin (cosmetic) whose UV protective effect changes by heat, preferably whose UV protective effect improves by heat. Moreover, the present invention provides a sunscreen external preparation for skin (cosmetic) whose UV protective effect improves by heat and which is identified by the screening method.

EXAMPLES

Hereinafter, the present invention is described in further detail with reference to examples. However, the present invention is not limited to these examples at all.

Two kinds of sunscreen cosmetics ((a) and (b)) having different compositions were prepared. A sample of each external agent (2 mg/cm$^2$) was applied to a plurality of skin-substitutive membranes (S-plates) and dried.

A part of each of the skin-substitutive membranes on which the sample coating films of (a) and (b) respectively were formed was left to stand in a thermostatic chamber (36.4° C.) for a predetermined time. The UV protective effect (absorbance) of each sample was measured after heat treatment.

With respect to each of the samples of (a) and (b), a change in the UV protective effect (absorbance) after heating was calculated according to the following equation based on the UV protective effect of a non-heated sample as 100.

Change in UV protective effect=("absorbance after heating"/"absorbance without heating")×100    [Expression 2]

Each of the UV protective effects was calculated using a value obtained by integrating absorbance over a wavelength region from 280 to 400 nm. Results are shown in the graph in FIG. 3.

Figure 3:
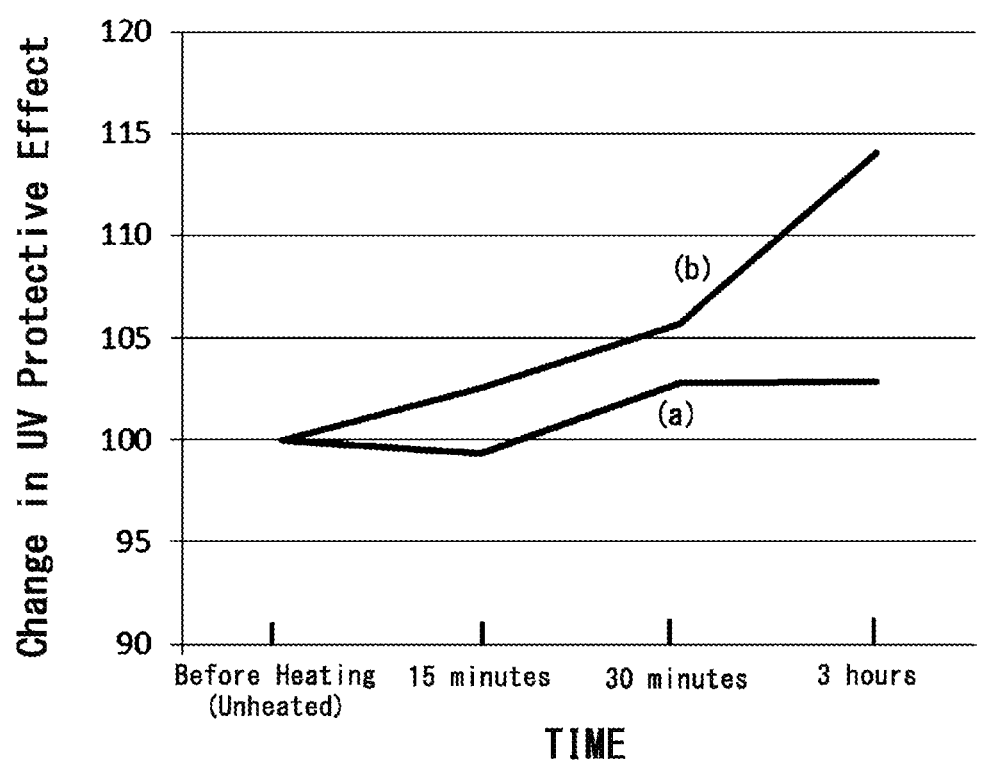
FIG. 3 is a graph showing a temporal change of a UV protective effect of a sunscreen cosmetic evaluated according to the method of the present invention.

As shown in FIG. 3, while almost no change in the UV protective effect due to heat was observed in sample (a), the UV protective effect significantly improved as the heating time increased in sample (b).

That is, by virtue of using the evaluation method of the present invention, a sunscreen cosmetic having a conventionally unknown new property of having a UV protective effect which is improved by heat can be accurately found. That is, the evaluation method of the present invention can be used as a method for screening a unburn-preventing cosmetic having a property of having a UV protective effect which is changed by heat.

DESCRIPTION OF MARKS

1: sample, 2: base body, 10: shielding material, 20: infrared lamp

The invention claimed is:

1. An evaluation method of an external preparation for skin, comprising:
   (1) forming a first coating film of an external preparation for skin on a first region of a base body;
   (2) subjecting the first coating film of the external preparation for skin to heat treatment carried out in an environment shielded from UV rays; and
   (3) measuring a protective effect against a UV ray of the first coating film of the external preparation for skin subjected to the heat treatment.

2. The evaluation method according to claim 1, wherein the measuring the protective effect against the UV ray includes at least one selected from a group consisting of SPF measurement, UVAPF or PFA measurement, critical wavelength measurement, absorbance measurement, transmittance measurement, and a test method comparing any UV protective effect.

3. The evaluation method according to claim 1, which is conducted in-vivo.

4. The evaluation method according to claim 3, wherein the heat treatment is carried out at a temperature higher than a body surface temperature and not higher than 45° C. for not shorter than one minute.

5. The evaluation method according to claim 4, further comprising:
   (1A) forming a second coating film of the external preparation for skin on a second region of the base body on which the first coating film is not formed at almost the same time as the forming (1);
   (2A) keeping the second coating film at ordinary temperature for a time period identical to a time period during which the subjecting (2) is performed; and
   (3A) measuring a UV protective effect of the second coating film at almost the same time as the measuring (3).

6. The evaluation method according to claim 5, wherein the base body is a predetermined site of skin of an animal, and the heat treatment is carried out by irradiation with an infrared ray.

7. The evaluation method according to claim 6, wherein the animal is a human, the predetermined site is a region between a shoulder blade and a waist of a back, the coating film of the external preparation for skin in the forming (1) is formed on one heating site out of two sites into which the region between the shoulder blade and the waist is divided, and the coating film of the other sample in the forming (1A) is formed on the other non-heating site out of the two sites.

8. The evaluation method according to claim 7, comprising separating the one heating site out of the two sites into which the region between the shoulder blade and the waist is divided from the other non-heating site by a shielding material before the subjecting (2) and the keeping (2A).

9. The evaluation method according to claim 1, which is conducted in-vitro.

10. The evaluation method according to claim 9, wherein the heat treatment is carried out at a temperature of 30° C. to 70° C. for one minute or longer.

11. The evaluation method according to claim 9, wherein the base body is a skin-substitutive membrane made of resin.

12. The evaluation method according to claim 9, wherein the heat treatment is carried out by
   (A) leaving a sample to which the external preparation for skin is applied to stand in a thermostatic chamber, or
   (B) irradiation with an infrared ray.

13. The evaluation method according to claim 9, further comprising measuring the UV protective effect of the coating film on the base body after the forming (1).

14. A screening method of a sunscreen cosmetic, comprising:
   identifying a sunscreen cosmetic having a UV protective effect which is improved by heat by conducting the evaluation method according to claim 1, and
   subsequently comparing a UV protective effect of a heated sample coating film and a UV protective effect of an unheated sample coating film.

15. A sunscreen cosmetic having a UV protective effect which is improved by heat, the sunscreen cosmetic identified by the screening method according to claim 14.

16. An in vivo evaluation method of an external preparation for skin, comprising:
   (1) forming a first coating film of an external preparation for skin on a first region of a base body;
   (2) subjecting the first coating film of the external preparation for skin to heat treatment;
   (3) measuring a protective effect against a UV ray of the first coating film of the external preparation for skin subjected to the heat treatment;
   (1A) forming a second coating film of the external preparation for skin on a second region of the base body on which the first coating film is not formed at almost the same time as the forming (1);
   (2A) keeping the second coating film at ordinary temperature for a time period identical to a time period during which the subjecting (2) is performed; and
   (3A) measuring a UV protective effect of the second coating film at almost the same time as the measuring (3).

* * * * *